United States Patent
Tai et al.

(10) Patent No.: US 7,812,953 B2
(45) Date of Patent: Oct. 12, 2010

(54) MIXTURE IDENTIFICATION SYSTEM

(75) Inventors: Makoto Tai, Tokyo (JP); Takafumi Izumiya, Tokyo (JP); Tsuyoshi Futamura, Tokyo (JP); Shigeyuki Shinohara, Tokyo (JP)

(73) Assignee: Japan Tobacco Inc., Tokyo (JP)

( * ) Notice: Subject to any disclaimer, the term of this patent is extended or adjusted under 35 U.S.C. 154(b) by 95 days.

(21) Appl. No.: 12/153,242

(22) Filed: May 15, 2008

(65) Prior Publication Data

US 2008/0316483 A1 Dec. 25, 2008

Related U.S. Application Data

(63) Continuation of application No. PCT/JP2006/322282, filed on Nov. 8, 2006.

(30) Foreign Application Priority Data

Nov. 16, 2005 (JP) .............................. 2005-331531

(51) Int. Cl.
 *G01N 21/25* (2006.01)
(52) U.S. Cl. ......................................... 356/419; 356/51
(58) Field of Classification Search ............ 250/339.07, 250/339.11; 356/419
 See application file for complete search history.

(56) References Cited

U.S. PATENT DOCUMENTS

| 6,657,722 B1 | 12/2003 | Nagayoshi et al. | |
|---|---|---|---|
| 6,667,802 B2* | 12/2003 | Faus et al. | 356/300 |
| 6,836,325 B2* | 12/2004 | Maczura et al. | 356/328 |
| 2002/0039185 A1* | 4/2002 | Sato et al. | 356/429 |
| 2003/0197126 A1* | 10/2003 | Sato et al. | 250/339.11 |
| 2005/0029469 A1* | 2/2005 | Schroder et al. | 250/458.1 |
| 2005/0143483 A1 | 6/2005 | Sanuki et al. | |
| 2006/0139644 A1* | 6/2006 | Kahn et al. | 356/406 |

FOREIGN PATENT DOCUMENTS

| CA | 2374153 A1 | 12/2000 |
|---|---|---|
| JP | 10-104154 A | 4/1998 |
| JP | 10-260027 A | 9/1998 |
| JP | 11-326181 A | 11/1999 |
| JP | 2001-281159 A | 10/2001 |
| JP | 2002-28544 A | 1/2002 |
| JP | 2005-37398 A | 2/2005 |
| JP | 2005-208046 A | 8/2005 |
| SU | 1109597 A | 8/1984 |
| UA | 84754 C2 | 3/2004 |
| WO | WO 00/74504 A1 | 12/2000 |
| WO | WO00/79247 A1 | 12/2000 |

* cited by examiner

*Primary Examiner*—Kara E Geisel
(74) *Attorney, Agent, or Firm*—Birch Stewart Kolasch & Birch, LLP

(57) ABSTRACT

A mixture identification system for detecting foreign matter admixed in a tobacco material includes a conveyor for conveying the material, an irradiation device for irradiating infrared light toward an inspection line extending across the conveyor, an infrared camera device for receiving the infrared light reflected from the tobacco material passing across the inspection line and outputting image data of the material based on the received infrared light, and a discrimination circuit for detecting foreign matter in the material based on the output from the camera device. The infrared camera device has infrared filters for receiving the infrared light reflected from the tobacco material and allowing only respective specific wavelengths to pass therethrough, and optical line sensors for receiving the infrared light passed through the respective filters.

14 Claims, 11 Drawing Sheets

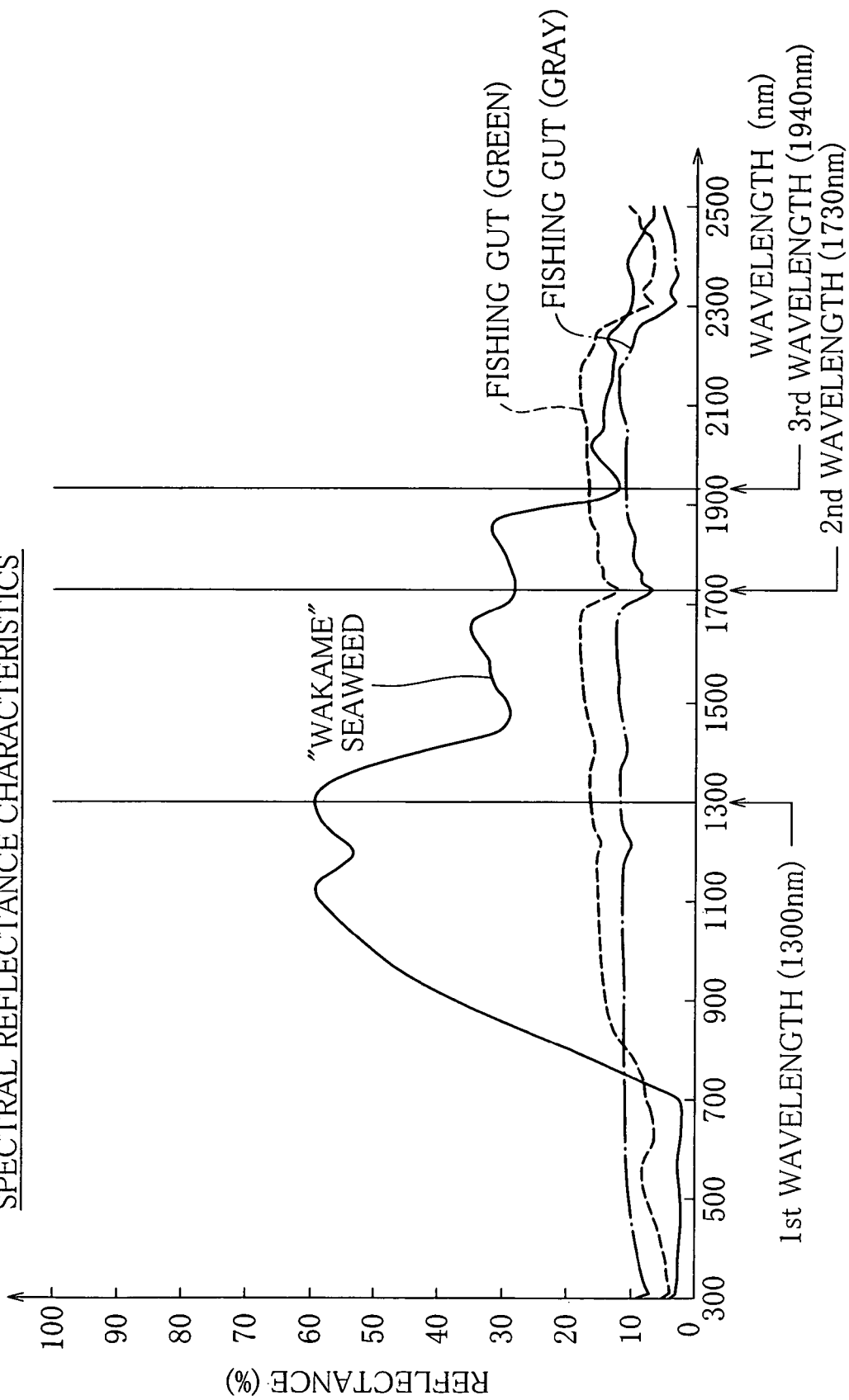

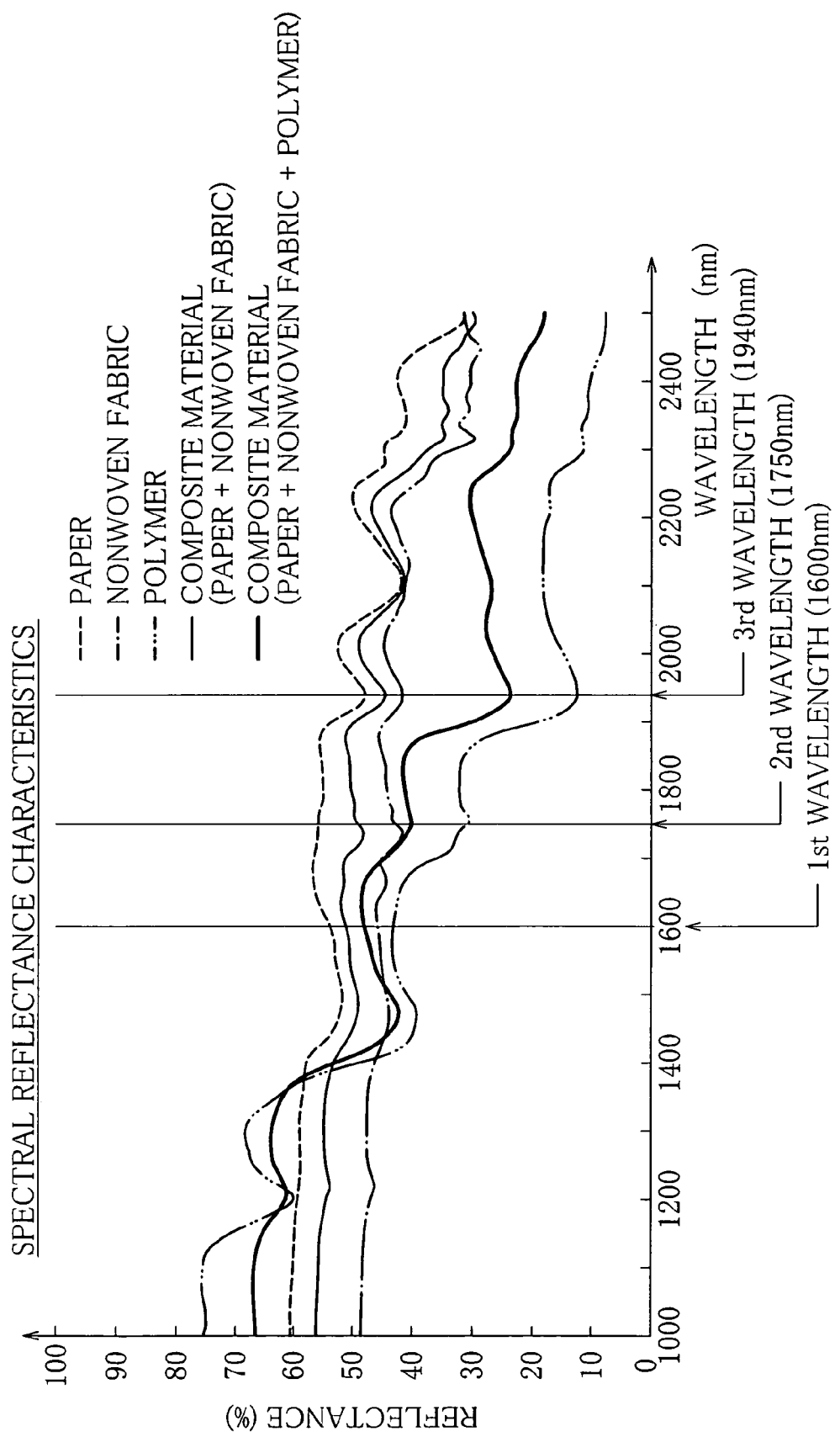

MIXTURE IDENTIFICATION SYSTEM

TECHNICAL FIELD

The present invention relates to identification systems for identifying a target material from a mixture containing a plurality of different materials of nearly the same color. More particularly, the invention relates to a mixture identification system applicable to detection of foreign matter where the mixture contains a material and foreign matter, as well as to identification of the distribution or arrangement of components where the mixture is a composite material comprising a plurality of different components.

BACKGROUND ART

The mixture identification system is used, for example, to detect foreign matter admixed in a material, and such detection apparatus is disclosed in Patent Document 1 identified below. In the apparatus disclosed in Patent Document 1, near-infrared light is irradiated onto tobacco leaves as a material, namely, tobacco material, and the reflected light from the tobacco material is captured using a near-infrared CCD camera to obtain image data. The image data is processed, and based on the processing results, foreign matter admixed in and having nearly the same color as the tobacco material is detected.

[Patent Document 1] Unexamined Japanese Patent Publication No. 2002-28544 (see [0016] to [0019] and FIG. 1)

More specifically, the detection apparatus of Patent Document 1 extracts near-infrared light with specific wavelengths (1.58 μm, 1.73 μm) from the infrared light reflected from the tobacco material and, based on the reflectance derived from the extracted near-infrared light, determines whether the object that reflected the extracted near-infrared light is the tobacco material or foreign matter. The extracted near-infrared light exhibits distinctive reflectance with respect to the tobacco material, and therefore, this technique cannot be applied to detection of foreign matter admixed in materials other than the tobacco material. Accordingly, the detection apparatus of Patent Document 1 lacks versatility.

Also, the detection apparatus of Patent Document 1 includes a spectroscope for extracting, that is, separating near-infrared light with the specific wavelengths from the light reflected from the tobacco material. The spectroscope includes a prism and a plurality of optical filters. With this type of spectroscope, it is not easy to modify the specification of the spectroscope when near-infrared light with wavelengths different from the specific wavelengths is to be extracted.

Further, the near-infrared CCD camera is adapted to intermittently acquire an image of the tobacco material while the tobacco material is being conveyed, and the image data thus obtained is processed separately on a frame-by-frame basis. Accordingly, in order to detect foreign matter admixed in the tobacco material without fail, the speed of conveying the tobacco material must be slowed, requiring much time for the detection of foreign matter. The detection apparatus of Patent Document 1 is therefore not suited for materials whose foreign matter needs to be detected at higher speeds.

When the tobacco material is imaged frame by frame, moreover, near-infrared light is irradiated unevenly onto the tobacco material within a frame, and if part of the tobacco material is shaded, then foreign matter cannot be detected with accuracy. It is, however, not easy to irradiate near-infrared light uniformly onto the tobacco material within a frame.

DISCLOSURE OF THE INVENTION

It is therefore an object of the present invention to provide a mixture identification system capable of high-speed and high-accuracy detection/identification of target materials in a variety of mixtures obtained by mixing together materials of nearly the same color.

To achieve the object, a mixture identification system according to the present invention comprises: conveying means for conveying a mixture along a predetermined conveyance path, the mixture containing a plurality of different materials of nearly identical color; an irradiation device including an inspection line extending across the conveyance path, the irradiation device being adapted to irradiate infrared light toward the mixture located on the inspection line; an infrared camera device for receiving the infrared light reflected from the mixture and outputting image data of the mixture based on the received infrared light; and a discrimination circuit for identifying a target material contained in the mixture, based on the output from the infrared camera device. The infrared camera device includes: a spectral mirror for separating the received infrared light into light beams of respective different wavelength regions; a plurality of infrared filters for receiving the respective light beams and allowing only infrared light with respective specific wavelengths to pass therethrough, the specific wavelengths of infrared light causing the materials contained in the mixture to show a predetermined difference in reflectance when irradiated onto the mixture and reflected by the respective materials; and a plurality of optical line sensors for receiving the infrared light beams passed through the respective infrared filters, each of the optical line sensors including a large number of light receiving elements so arranged as to receive the infrared light reflected from the mixture on the inspection line and individually generating, as the image data, electrical signals corresponding to amounts of the infrared light received.

In this identification system, first, the specific wavelengths of infrared light that are effective in detecting or identifying a target material are selected on the basis of the combination of materials constituting the mixture. Subsequently, a spectral mirror and infrared filters matching the selected specific wavelengths of infrared light are attached to the infrared camera device.

After the setting is completed, infrared light is irradiated from the irradiation device onto the inspection line on the conveyance path. As the mixture passes across the inspection line, the infrared light reflected from the mixture is received by the individual optical line sensors of the infrared camera device through the spectral mirror and the infrared filters, and the optical line sensors individually output image data of the mixture to the discrimination circuit. Based on the received image data, the discrimination circuit detects or identifies the target material contained in the mixture.

Thus, the infrared filters to be used are selected in accordance with the kind of mixture. Accordingly, the mixture identification system of the present invention can detect foreign matter included in a variety of mixtures or can identify a target material from among materials forming the mixture and thus has high versatility.

Also, the infrared camera device includes multiple optical line sensors each adapted to acquire an image of the mixture based on the infrared light reflected from the mixture passing across the inspection line. The detection of foreign matter or the identification of a target material can therefore be carried out at high speed.

Preferably, the infrared camera device may further include a compensation circuit for compensating for a difference in sensitivity between the light receiving elements of the individual optical line sensors. The compensation circuit has gains and offset values set with respect to the individual light receiving elements to correct the electrical signals from the respective elements.

Variation in sensitivity of the light receiving elements included in the individual optical line sensors is unavoidable, and it is also difficult to irradiate infrared light uniformly over the entire length of the inspection line by the irradiation device. Such variation of the sensitivity and nonuniformity of the irradiation are eliminated by the compensation circuit. The individual optical line sensors can therefore output accurate image data of the mixture, making it possible to detect foreign matter or identify the target material with accuracy.

The infrared camera device may further include a calibration plate capable of uniformly reflecting infrared light, and a guide for guiding movement of the calibration plate between an operative position located on the inspection line and a rest position remote from the inspection line.

When the calibration plate is set in the operative position, the infrared light from the irradiation device is uniformly reflected by the calibration plate toward the optical line sensors. Based on the reflected light, the gains and offset values assigned to the respective light receiving elements of the individual optical line sensors are set with precision. As a result, the infrared camera device can output accurate image data of the mixture.

The setting of the gains and offset values is carried out before the infrared camera device is put to use or at regular intervals.

On the other hand, the irradiation device includes a pair of lamp units for irradiating infrared light onto the inspection line. The lamp units are arranged upstream and downstream, respectively, of the inspection line as viewed in the conveying direction of the mixture.

When the mixture passes across the inspection line, the pair of lamp units irradiate infrared light onto the mixture from both sides of the inspection line, that is, from the upstream and downstream sides as viewed in the conveying direction of the mixture, so that the mixture is not shaded at all. Accordingly, the infrared light is reflected from the entire inspected region of the mixture, and the reflected infrared light is received without fail by the individual optical line sensors. The identification system can therefore detect foreign matter or identify the target material with higher accuracy.

Specifically, each lamp unit may include a straight tube-type halogen lamp extending parallel with the inspection line and adapted to emit infrared light, and a reflector for reflecting the infrared light from the halogen lamp toward the inspection line.

In the case of a straight tube-type halogen lamp, the infrared light emitted from the opposite end portions of the halogen lamp is weaker than that emitted from the central portion of the lamp. The straight tube-type halogen lamp is thus unable to irradiate infrared light uniformly over the entire length of the inspection line. Since the infrared camera device includes the compensation circuit, however, no inconvenience arises out of nonuniform irradiation of the infrared light.

The irradiation device may further include a lamp housing containing the pair of lamp units and having an opening for allowing the infrared light emitted from the pair of lamp units to pass therethrough toward the inspection line, a glass window closing the opening and allowing the infrared light to transmit therethrough, and a cooling unit for cooling air in the lamp units.

Specifically, the cooling unit supplies cooling air into the lamp units and keeps the pressure in the lamp units higher than the external pressure.

The cooling air circulated through the lamp housing serves not only to reduce heat radiated from the lamp housing toward the mixture but to prevent overheating of the irradiation device and the identification system as well as entry of dust into the lamp housing. Accordingly, the inner surface of the glass window can always be kept clean and the infrared light transmitted through the glass window is not adversely affected by dust.

Preferably, the irradiation device may further include an air injection unit for producing a flow of air along the outer surface of the glass window. The air injection unit prevents dust from adhering to the outer surface of the glass window, whereby the outer surface of the glass window is also kept clean.

The irradiation device may further include a slide mechanism permitting the pair of lamp units to be pulled out of the lamp housing. The slide mechanism supports the pair of lamp units in such a manner that the lamp units are slidable in a direction parallel with the inspection line. With this arrangement, the halogen lamps of the individual lamp units can be replaced with new ones with the lamp units pulled out of the lamp housing, facilitating the replacement of the halogen lamps.

BRIEF DESCRIPTION OF THE DRAWINGS

FIG. 12 is a graph showing spectral reflectance characteristics of wakame seaweed and foreign matter with respect to infrared light.

FIG. 13 is a graph showing spectral reflectance characteristics of composite materials, namely, a diaper and a sanitary item, and their components with respect to infrared light.

BEST MODE OF CARRYING OUT THE INVENTION

Figure 1:
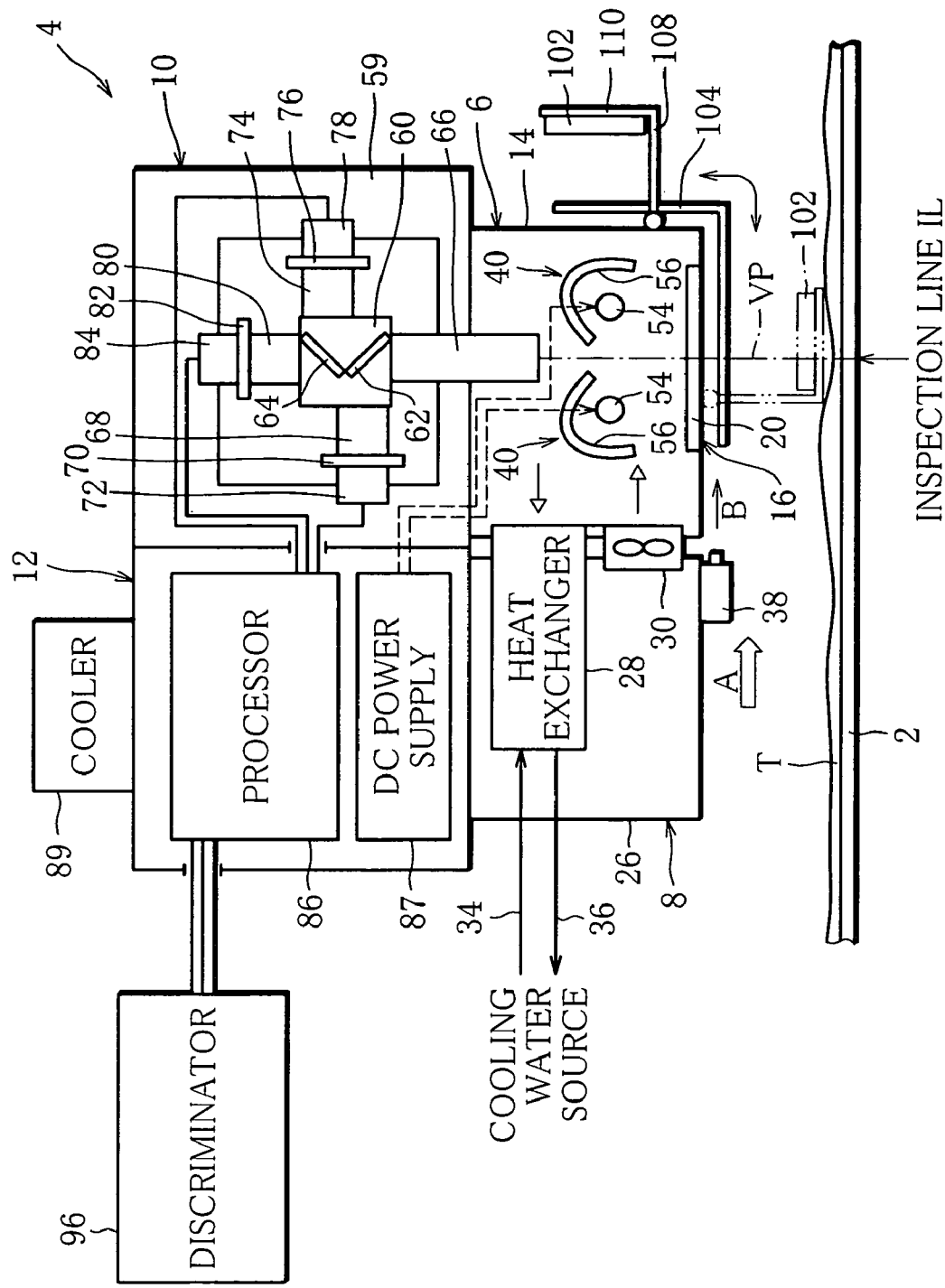
FIG. 1 shows a schematic construction of a mixture identification system according to one embodiment of the present invention.

FIG. 1 shows a mixture identification system which is used, for example, to detect foreign matter admixed in a tobacco material.

The identification system shown in FIG. 1 has a conveyance path for tobacco material T, namely, a conveyor 2. The conveyor 2 extends horizontally and conveys the tobacco material T at a predetermined speed in the direction indicated by arrow A in FIG. 1. The tobacco material T denotes tobacco leaves of one kind of domestic tobacco, burley tobacco, Oriental tobacco and flue-cured tobacco or a mixture of these tobacco leaves. The tobacco material T is thinly spread on the conveyor 2.

In general, there is a possibility that foreign matter is admixed in the cropped tobacco material T, and possible foreign matter includes synthetic resin used in wrappers or strings for packing tobacco leaves, urethane foam used in boxes for packing tobacco leaves, and fragments of moisture-proof paper used as lining of packing boxes. The tobacco material T is therefore a mixture of tobacco leaves and such foreign elements.

A camera assembly 4 is arranged above the conveyor 2 and includes an irradiation device 6, a cooling device 8, an infrared camera device 10, and a signal converter 12.

The irradiation device 6 is located at a lower part of the camera assembly 4 and includes a lamp housing 14. The lamp housing 14 has a lower surface facing the conveyor 2 and provided with a heat-resistant glass window 16.

Figure 2:
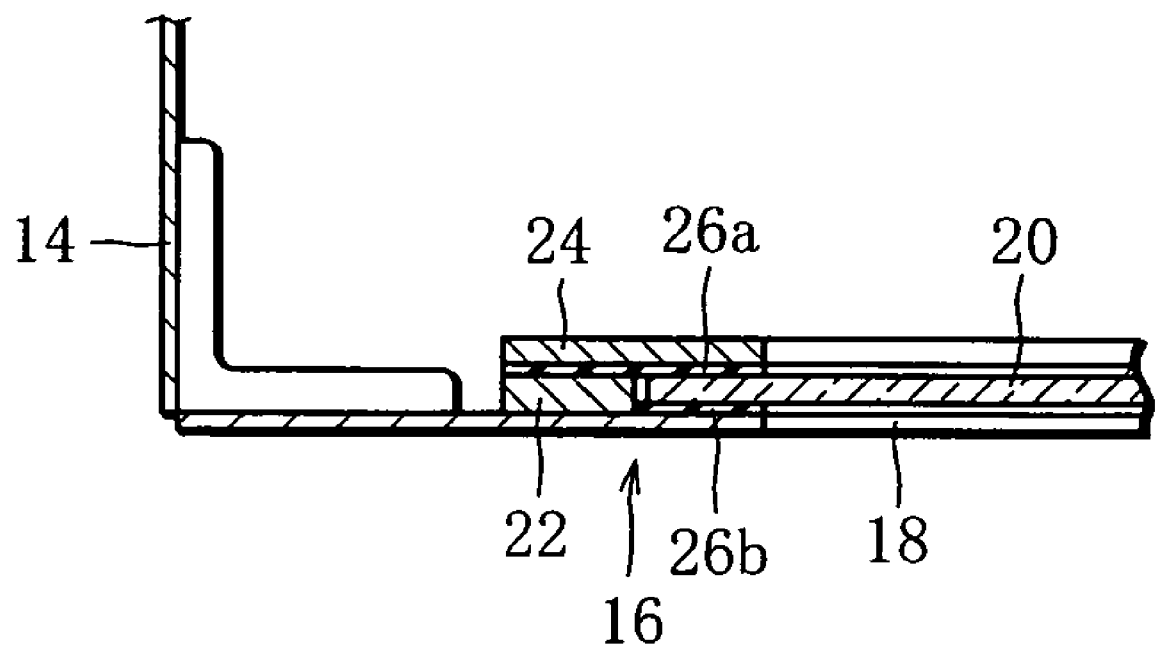
FIG. 2 is a sectional view of part of a lamp housing shown in FIG. 1.

As shown in FIG. 2, the glass window 16 includes an opening 18 formed in the lower surface of the lamp housing 14, and a heat-resistant glass plate 20 closing the opening 18 and located inside the lamp housing 14. More specifically, the glass window 16 further includes a window frame 22 arranged inside the lamp housing 14 and surrounding the glass plate 20, a press plate 24 for pressing the window frame 22 and the glass plate 20, packing 26a sandwiched between the press plate 24 and the window frame 22 or the glass plate 20, and packing 26b sandwiched between the glass plate 20 and the inner surface of the lamp housing 14.

On the left of the lamp housing 14 as viewed in FIG. 1, the cooling device 8 is arranged adjacent to the lamp housing 14 and has a cooling box 26. The cooling box 26 and the lamp housing 14 are connected to each other through a heat exchanger 28 and a circulation fan 30. The heat exchanger 28 and the circulation fan 30 are used as a cooling unit for the irradiation device 6.

The heat exchanger 28 is connected with a cooling water supply pipe 34 and a return pipe 36. The pipes 34 and 36 extend through the cooling box 26 to a source of cooling water. The cooling water source supplies cooling water of a constant temperature to the heat exchanger 28 through the supply pipe 34 and also receives the cooling water returned from the heat exchanger 28 through the return pipe 36. Namely, the cooling water source causes the cooling water to circulate through the heat exchanger 28, which in turn cools the air in the cooling box 26 so that the cooling air temperature may be kept at a fixed temperature or below.

The circulation fan 30 causes the cooling air in the cooling box 26 to be introduced into the lamp housing 14. The air in the lamp housing 14, on the other hand, is returned to the cooling box 26 through the heat exchanger 28. Thus, the cooling air is allowed to circulate between the cooling box 26 and the lamp housing 14.

The circulation fan 30 supplies the cooling air to the interior of the lamp housing 14 so that the internal pressure of the lamp housing 14 may always be kept higher than the air pressure outside the housing 14. Thus, the interior of the lamp housing 14 remains in a pressurized state, preventing the outside air from entering the lamp housing 14. Consequently, a situation where dust accumulates on the glass window 16, that is, the inner surface of the glass plate 20, does not occur.

Further, an air injection unit 38 is attached to the lower surface of the cooling box 26. The air injection unit 38 is supplied with compressed air from a pneumatic pressure source (not shown) and injects the compressed air along the outer surface of the glass plate 20, as indicated by arrow B in FIG. 1. The jet of the compressed air prevents dust from adhering to the outer surface of the glass plate 20, and as a result, the inner and outer surfaces of the glass plate 20 can be kept clear of dust.

As is clear from FIG. 1, a pair of lamp units 40 are arranged inside the lamp housing 14. The interior of the lamp housing 14 is shown in detail in FIG. 3.

The lamp housing 14 extends in a direction across the conveyor 2 and is open at opposite ends. These openings can be closed with respective lids (not shown) which are, for example, hinged on the lamp housing 14.

A pair of unit holders 42 are arranged in the lamp housing 14 and extend inside the lamp housing 14 in a direction across the conveyor 2. Holder brackets 44 are disposed at respective opposite ends of the individual unit holders 42. The holder brackets 44 support the respective ends of the pair of unit holders 42 and are vertically movably mounted on the lamp housing 14.

More specifically, each holder bracket 44 extends in the traveling direction of the conveyor 2 across the corresponding opening of the lamp housing 14 and has opposite ends supported on the lamp housing 14 by means of screw blocks 46. Each screw block 46 includes a block 48 secured to the corresponding end face of the lamp housing 14 and having a vertically extending threaded hole, and a screw rod 50 screwed into the threaded hole and penetrating through the block 48. The opposite ends of each holder bracket 44 are supported on the upper ends of the respective screw rods 50.

The screw blocks 46 permit adjustment of the vertical position of the holder brackets 44, namely, the height of the unit holders 42. After the height of the unit holders 42 is adjusted, the holder brackets 44 are fixed to the lamp housing 14 by setscrews (not shown).

Each unit holder 42 has a slide mechanism at a lower part thereof, and the slide mechanism includes a slider 52. The slider 52 is slidable relative to the unit holder 42 in the longitudinal direction thereof, that is, in a direction across the conveyor 2, and has exposed end faces not covered with the unit holder 42.

A lamp unit 40 is mounted on each slider 52. The lamp unit 40 includes a straight tube-type halogen lamp 54 and a reflector 56 covering the halogen lamp 54. The reflector 56 reflects infrared light emitted from the halogen lamp 54 so as to be directed to the conveyor 2. The halogen lamp 54 and the reflector 56 extend in a direction across the conveyor 2 and cover the entire width of the conveyor 2.

When one of the openings of the lamp housing 14 is open, each lamp unit 40 can be pulled out of the housing 14 together with the slider 52 through the opening, and the lamp unit 40 thus pulled out can be again put back into a given position inside the lamp housing 14. To make it easier to pull out and push back the lamp unit 40, a handle 58 is attached to each end face of the slider 52, as shown in FIG. 3.

Figure 3:
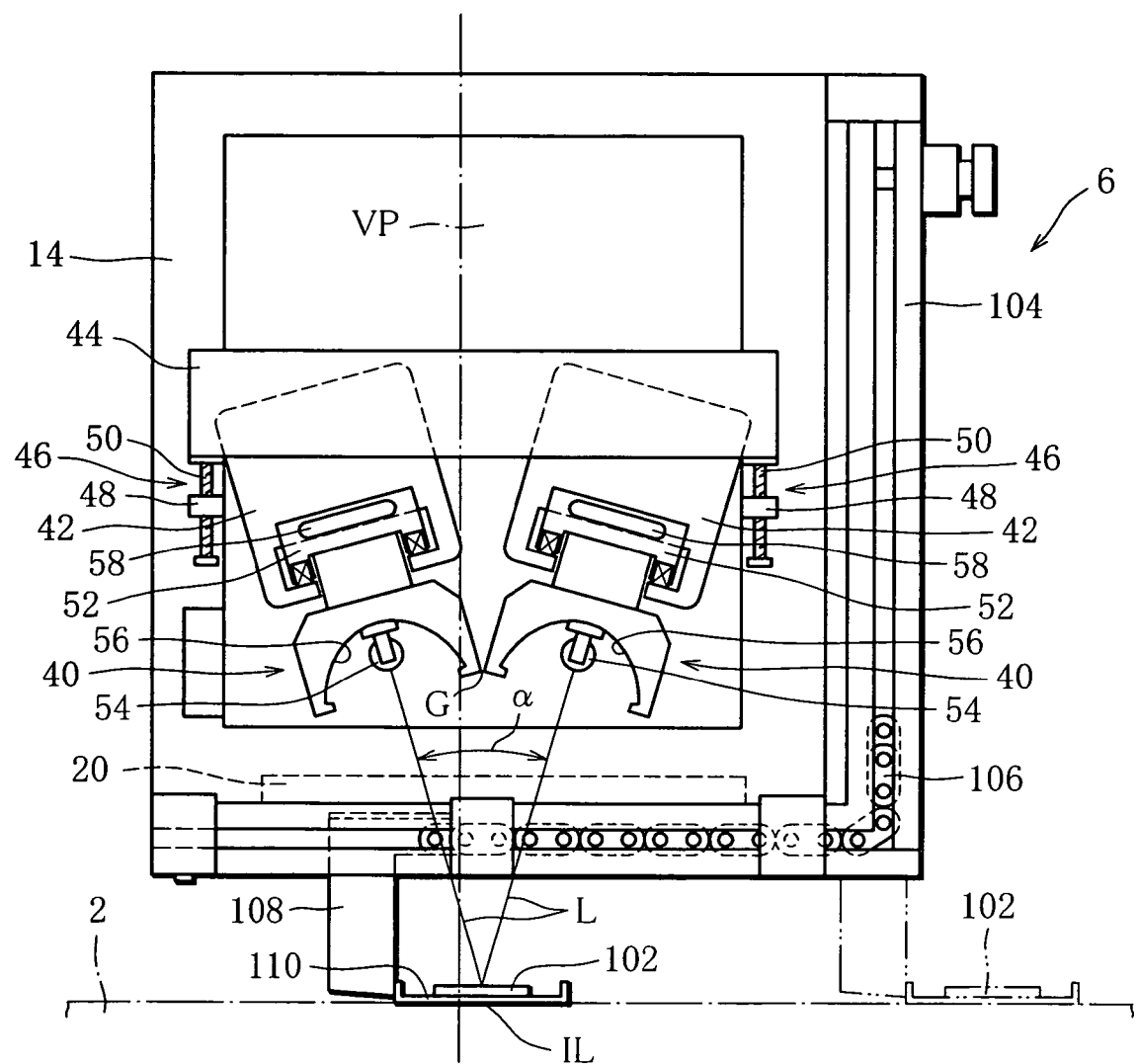
FIG. 3 shows in detail the interior of the lamp housing shown in FIG. 1.

As clearly shown in FIG. 3, the pair of lamp units 40 are arranged on upstream and downstream sides, respectively, of the conveyer 2 with an inspection line IL located therebetween. The inspection line IL is set at a predetermined position on the conveyor 2 and extends in a direction across the conveyor 2. The pair of lamp units 40 emit infrared light from their respective halogen lamps 54. The emitted infrared light reaches the inspection line IL directly or indirectly by being reflected by the respective reflectors 56, so that the infrared light is converged onto the inspection line IL.

More specifically, provided that a plane connecting between the axis of the halogen lamp 54 of each lamp unit 40 and the inspection line IL is L and that a vertical plane containing the inspection line IL is VP as shown in FIG. 3, each plane L is slanted at a predetermined angle with respect to the vertical plane VP and an angle α between the planes L is, for example, 60°.

The vertical plane VP extends through a gap G between the pair of lamp units 40. Accordingly, when the infrared light from the pair of lamp units 40 is irradiated through the glass window 16 onto the tobacco material T on the conveyor 2, part of the infrared light reflected from the tobacco material T is allowed to transmit through the glass window 16 and travel upward through the gap between the lamp units 40 along the vertical plane VP.

Referring again to FIG. 1, the infrared camera device 10 has a camera housing 59 placed on the lamp housing 14. A mirror box 60 is arranged inside the camera housing 59 and accommodates, as a spectral mirror, a pair of dichroic mirrors 62 and 64. The mirrors 62 and 64 are disposed in the form of the letter V directed sideways with the mirror 62 positioned beneath the mirror 64. A lens casing 66 extends downward from the mirror box 60 and has a lower end portion projecting into the lamp housing 14.

The dichroic mirrors 62 and 64 and the lens casing 66 are positioned on the vertical plane VP; therefore, the infrared light reflected by the tobacco material T and directed upward along the vertical plane VP is allowed to enter the dichroic mirror 62 through the lens casing 66.

Of the infrared light incident on the dichroic mirror 62, infrared light with wavelengths longer than or equal to 1825 nm is reflected as a reflected beam by the dichroic mirror 62, and infrared light with wavelengths shorter than 1825 nm is transmitted through the dichroic mirror 62 as a transmitted beam. The reflected beam from the dichroic mirror 62 enters a lens casing 68 and impinges on an infrared filter 70. Of the reflected beam, only the infrared light with the wavelength 1940 nm is transmitted through the infrared filter 70 and allowed to enter an optical line sensor 72.

The transmitted beam from the dichroic mirror 62 is incident on the dichroic mirror 64. Of the transmitted beam, infrared light with wavelengths longer than or equal to 1625 nm is reflected as a reflected beam by the dichroic mirror 64, and infrared light with wavelengths shorter than 1625 nm is transmitted through the dichroic mirror 64 as a transmitted beam. The reflected beam from the dichroic mirror 64 enters a lens casing 74 and impinges on an infrared filter 76. The infrared filter 76 transmits only the infrared light with the wavelength 1720 nm therethrough, the transmitted infrared light being incident on an optical line sensor 78.

On the other hand, the transmitted beam from the dichroic mirror 64 enters a lens casing 80 and impinges on an infrared filter 82. The infrared filter 82 transmits only the infrared light with the wavelength 1550 nm therethrough and the thus transmitted infrared light impinges on an optical line sensor 84.

The infrared filters 70, 76 and 82 are detachably attached to the respective lens casings.

Each of the optical line sensors 72, 78 and 84 includes a large number of light receiving elements (not shown) arranged adjacent to each other in a row and each adapted to generate an electrical signal corresponding to the amount of the incident infrared light. More specifically, each optical line sensor extends in a direction across the conveyor 2 and has a length greater than or equal to the width of the conveyor 2. Accordingly, each optical line sensor can receive, with its light receiving elements, the corresponding wavelength of infrared light reflected from the entire inspected region of the tobacco material T on the inspection line IL.

The electrical signals generated by the light receiving elements of each of the optical line sensors 72, 78 and 84 are used as data for creating an image of the tobacco material T passing across the inspection line IL, and in this case, the electrical signal from each light receiving element corresponds to one pixel in the image obtained.

The dichroic mirrors 62 and 64 and the lens casings 66, 68, 74 and 80 individually extend in the width direction of the conveyor 2. Each dichroic mirror has a length greater than or equal to the width of the conveyor 2, and each lens casing has an aperture width greater than or equal to the width of the conveyor 2. Needless to say, each of the lens casings 66, 68, 74 and 80 has a focusing lens (not shown) and the like built therein.

The optical line sensors 72, 78 and 84 are electrically connected to the aforementioned signal converter 12. The signal converter 12 includes three processing circuits 86 for processing the electrical signals from the respective optical line sensors. The signal converter 12 further includes a direct-current power supply 87 connected to the individual halogen lamps 54 of the lamp units 40, and a cooler 89 arranged externally to a housing thereof. The cooler 89 is adapted to cool the interior of the signal converter 12.

Figure 4:
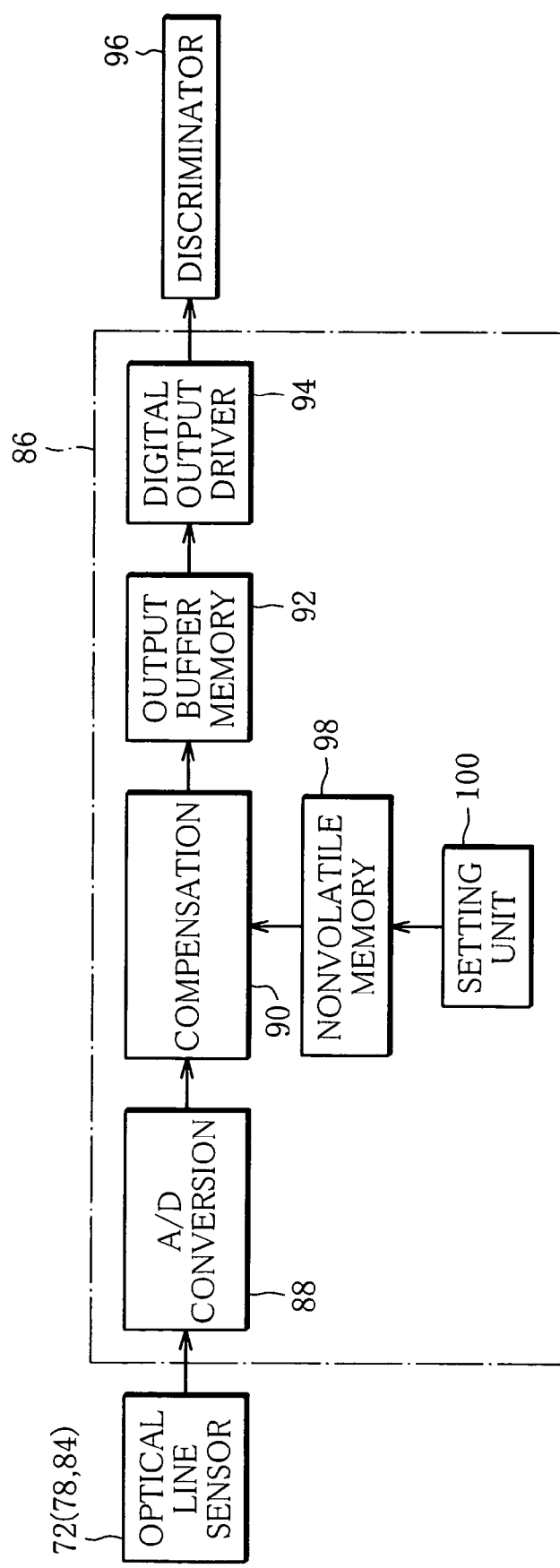
FIG. 4 is a block diagram of a processing circuit appearing in FIG. 1.

FIG. 4 shows an example of the processing circuit 86.

The processing circuit 86 has an A/D converter 88 electrically connected to the corresponding optical line sensor. The A/D converter 88 receives the analog signals generated by the individual light receiving elements of the corresponding optical line sensor, converts the received electrical signals to digital signals X, and supplies the obtained signals X to a subsequent compensator 90.

The compensator 90 corrects the individual electrical signals X associated with the respective light receiving elements to obtain corrected signals Y, and outputs the corrected electrical signals Y to an output buffer memory 92. The output buffer memory 92 outputs the electrical signals Y through a digital output driver 94 to a discrimination circuit 96 external to the signal converter 12.

In the following, the significance of correction of the electrical signals X will be explained in more detail.

The sensitivities of the individual light receiving elements to infrared light are uneven, and it is also difficult to uniformly irradiate the tobacco material T spread over the entire length of the inspection line IL with the infrared light emitted from the irradiation device 8. Thus, where a reference plate capable of uniformly reflecting infrared light is positioned on the inspection line IL, the electrical signals X generated by the respective light receiving elements of each optical line sensor show uneven levels, as indicated by the solid line in FIG. 5. The output levels of the electrical signals X represent the sensitivities of the respective light receiving elements to infrared light.

Figure 5:
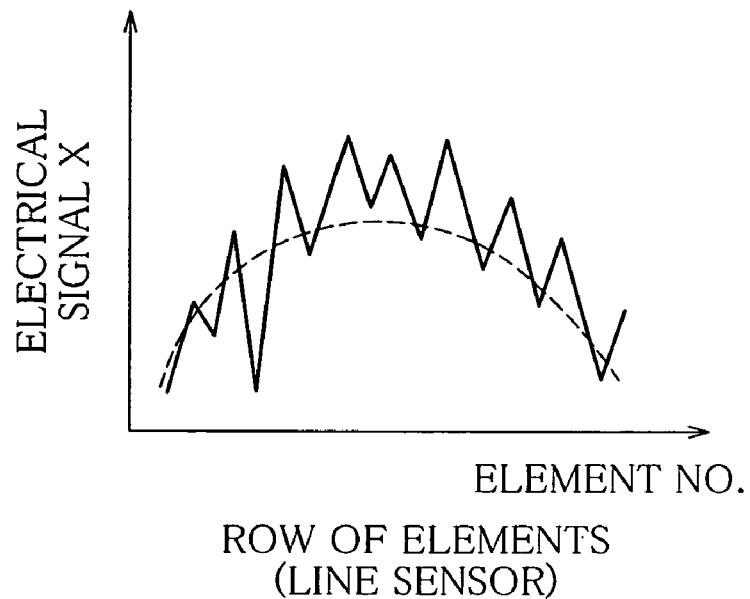
FIG. 5 is a graph showing variation in sensitivity of light receiving elements of an optical line sensor.

In FIG. 5, the broken line indicates the illuminance distribution of infrared light irradiated onto the inspection line IL from the irradiation device 8. Generally, the straight tube-type halogen lamp 54 has such a characteristic that the infrared light emitted from the opposite end portions of the lamp is weaker than that emitted from the central portion of same.

The electrical signals X from the respective light receiving elements are therefore corrected according to the correction equation below, to obtain the corrected electrical signals Y.

$$Y = \alpha X + \beta$$

where α and β represent a gain and offset value, respectively, specific to each individual light receiving element.

Figure 6:
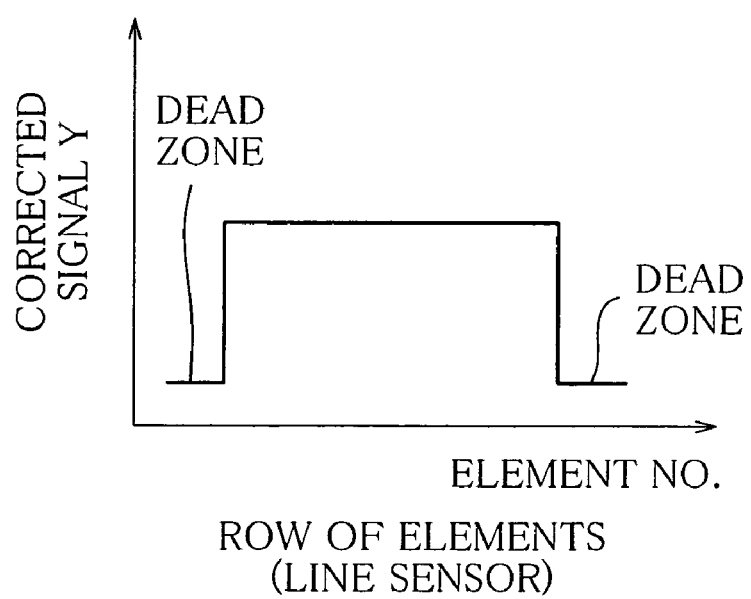
FIG. 6 is a graph illustrating a function of a compensator appearing in FIG. 4.

The gains α are values so determined as to compensate for variations of the output levels of the electrical signals X from the respective light receiving elements and are set in a manner specific to the respective elements. Once the individual light receiving elements of each optical line sensor are assigned respective appropriate gains α, the electrical signals Y output from the compensator 90 and associated with the respective light receiving elements have a fixed output level, as shown in FIG. 6.

On the other hand, the offset values β are set in order to eliminate the adverse influence of the infrared light reflected by a guide frame (not shown) extending on both sides of the conveyor 2. Specifically, the offset values β are assigned only to a predetermined number of light receiving elements located at the opposite end portions of each optical line sensor and are set to values large enough to cancel out the electrical signals X from these light receiving elements. Consequently, the electrical signals Y show an output distribution having a dead zone on either side, as shown in FIG. 6.

To enable the compensator 90 to carry out the aforementioned correction, the compensator 90 is electrically connected with a nonvolatile memory 98 storing the gains α and offset values β assigned to the respective light receiving elements. The gains α and offset values β associated with the respective light receiving elements are fetched from the memory 98 and applied to the corresponding electrical signals X by the compensator 90, whereby the electrical signals X are corrected according to the aforementioned equation and the corrected electrical signals Y are output from the compensator 90.

The gains α and the offset values β are stored in the memory 98 with the use of a setting unit 100. By using the setting unit 100, it is also possible to rewrite the gains α and offset values β stored in the memory 98.

In order to assign appropriate gains α to the respective light receiving elements of each optical line sensor, the infrared camera device 10 is provided with a calibration plate 102 used as the aforementioned reference plate, as shown in FIG. 1. The calibration plate 102 is positioned on the inspection line IL when necessary.

Figure 7:
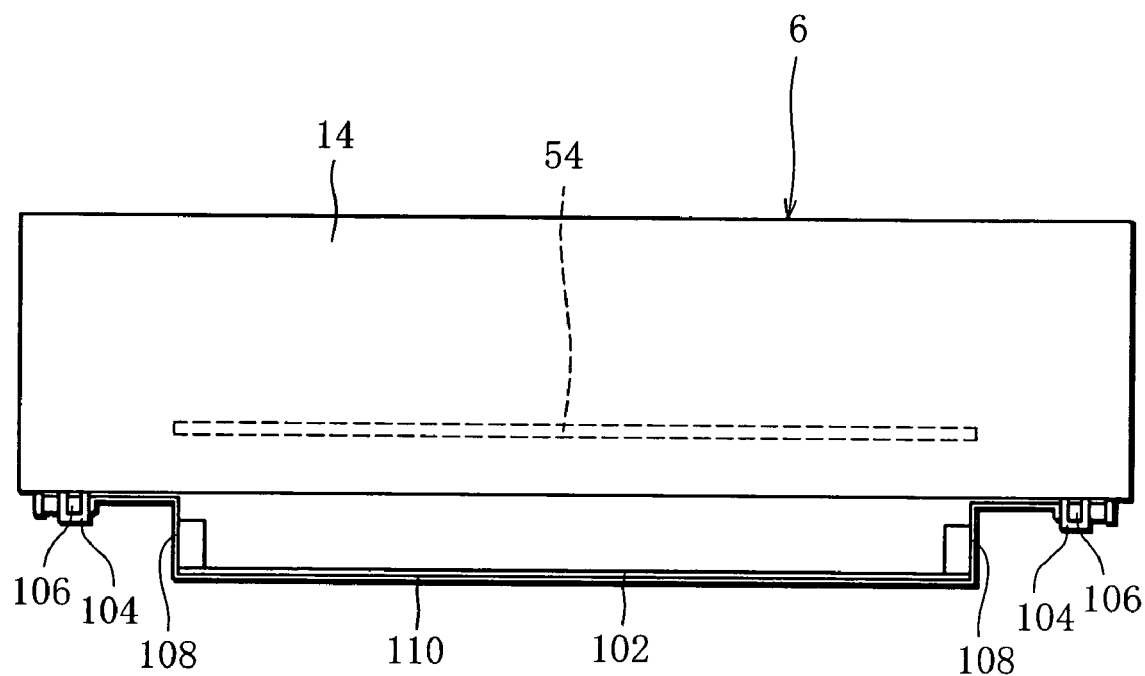
FIG. 7 is a side view of the lamp housing with a calibration plate set in an operative position.

More specifically, a pair of guide rails 104 are attached to the outer surface of the lamp housing 14, as shown in FIG. 3. The guide rails 104 are located at the respective opposite end portions of the lamp housing 14, taken in the direction across the conveyor 2. Each guide rail 104 is L-shaped and extends from the lower surface of the lamp housing 14 to a side wall of same. The guide rails 104 serve to guide the movement of respective chains 106, and brackets 108 are attached to the respective chains 106. The brackets 108 project outward from the lamp housing 14 and are connected to each other by a connecting plate 110. As is clear from FIG. 7, the connecting plate 110 extends in the longitudinal direction of the lamp housing 14 (in the width direction of the conveyor 2) and carries the calibration plate 102 on an upper surface thereof.

The calibration plate 102 is made of a material capable of uniformly reflecting infrared light and hardly susceptible to thermal deformation. For example, the calibration plate 102 is made of Teflon, PEEK, or ceramic.

When the calibration plate 102 is set in an operative position located on the inspection line IL, as shown in FIG. 3, the plate 102 uniformly reflects the infrared light emitted from the irradiation device 6. Accordingly, the infrared light reflected from the calibration plate 102 is received by the light receiving elements of the individual optical line sensors, and the gains a to be assigned to the respective light receiving elements are determined based on the output levels of the electrical signals X from the respective elements.

The calibration plate 102 is movable together with the chains 106 along the pair of guide rails 104. Thus, while the tobacco material T is being conveyed on the conveyor 2, as shown in FIG. 1, the calibration plate 102 can be set aside in a rest position close to the side wall of the lamp housing 14 so that the calibration plate 102 may not hinder the conveyance of the tobacco material T.

The calibration plate 102 is used not only for the aforementioned initial setting of the gains α but also for the resetting of the gains α which is carried out at regular intervals in consideration of aged deterioration in the sensitivity of the individual light receiving elements.

The discrimination circuit 96 mentioned above receives the outputs of the processing circuits 86, that is, image data $D1_n$, $D2_n$ and $D3_n$ obtained respectively based on the first wavelength (1550 nm), second wavelength (1720 nm) and third wavelength (1940 nm) of infrared light, and detects foreign matter admixed in the tobacco material T on the basis of the image data. The subscript "n" in the image data $D1_n$, $D2_n$ and $D3_n$ generically represents the element numbers of the light receiving elements of the respective optical line sensors.

The first to third wavelengths of infrared light are selected on the basis of the difference in reflectance between the tobacco material T and foreign matter with respect to infrared light such that the combination of the first to third wavelengths is best suited for detecting, namely, identifying the foreign matter from the tobacco material T.

This will be explained in more detail. Tobacco leaves as the tobacco material T have similar spectral reflectance characteristics indicated by solid lines $T_1$ to $T_4$ in FIG. 8, whereas foreign elements as the foreign matter have spectral reflectance characteristic indicated by broken line ($F_1$), dot-dash line ($F_2$) and dot-dot-dash line ($F_3$) in FIG. 8. In the graph, $T_1$ to $T_4$ indicate the spectral reflectance characteristics of domestic tobacco leaves, burley tobacco leaves, Oriental tobacco leaves and flue-cured tobacco leaves, respectively, and $F_1$ to $F_3$ indicate the spectral reflectance characteristics of the aforementioned foreign elements, namely, synthetic resin used in wrappers and strings, urethane foam and moisture-proof paper, respectively.

Figure 8:
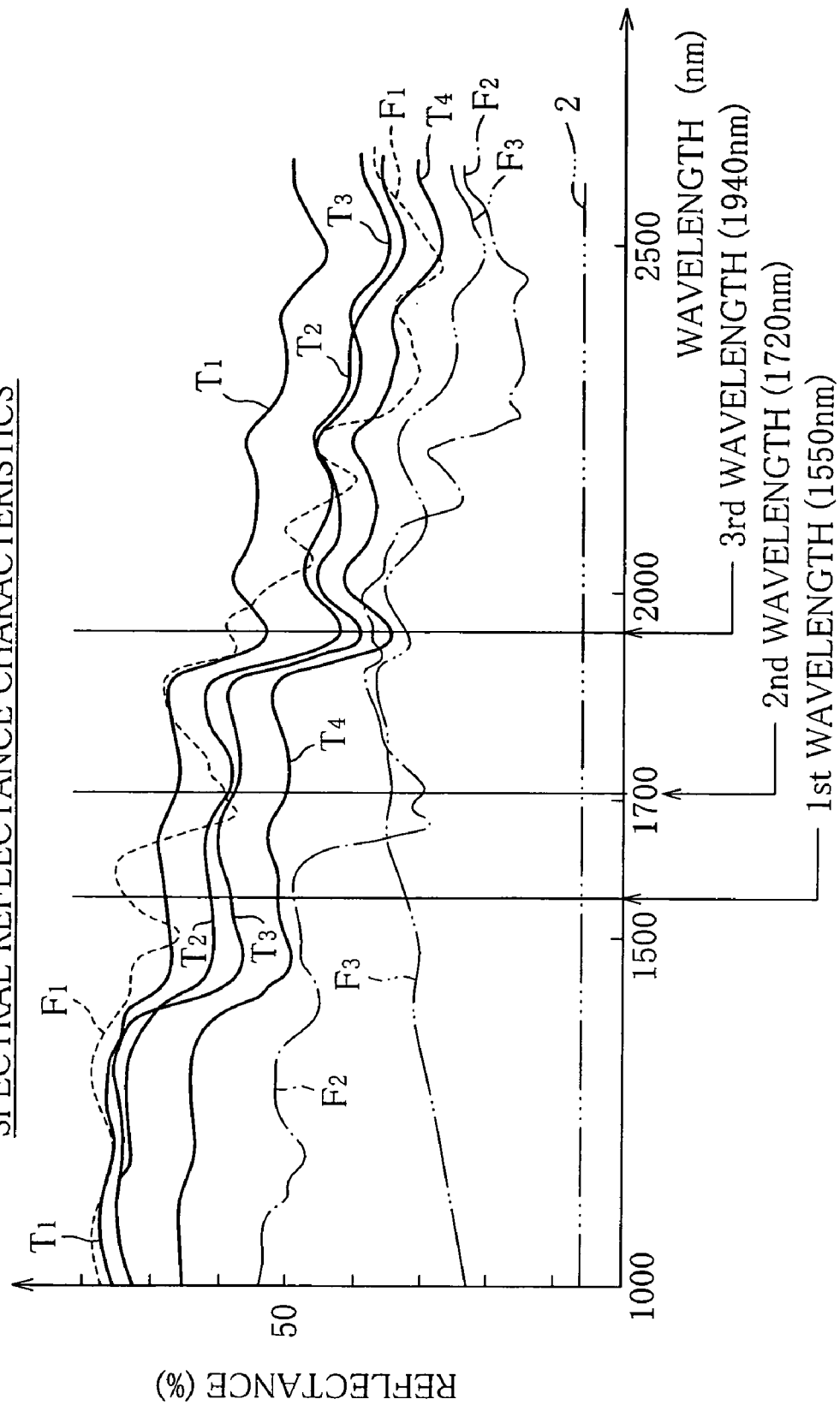
FIG. 8 is a graph showing spectral reflectance characteristics of tobacco material and foreign matter with respect to infrared light.

As is clear from FIG. 8, the reflectances of the tobacco materials $T_1$ to $T_4$ with respect to the first wavelength of infrared light evidently differ from those of the foreign elements $F_1$ to $F_3$ with respect to the same wavelength.

With respect to the second wavelength of infrared light, there is observed no clear difference between the reflectances of the tobacco materials $T_2$ and $T_3$ and that of the foreign element $F_1$. However, the reflectance of the tobacco material $T_1$ significantly differs from those of the foreign elements $F_2$ and $F_3$.

Further, with respect to the third wavelength of infrared light, there is no significant difference between the reflectances of the tobacco materials $T_3$ and $T_4$ and those of the foreign elements $F_2$ and $F_3$, but the reflectances of the tobacco materials $T_1$ and $T_2$ clearly differ from that of the foreign element $F_1$.

Accordingly, while the infrared light including the first to third wavelengths is reflected from the tobacco material T, the actual electrical signals Y are compared with allowable level ranges for the electrical signals Y corresponding to allowable reflectance ranges for the first to third wavelengths, whereby the foreign elements admixed in the tobacco material T can be detected, that is, identified by the discrimination circuit 96.

Specifically, the discrimination circuit 96 calculates ratios $R_1(=D1_n/D3_n)$ and $R_2(=D2_n/D3_n)$ of the aforementioned image data and, if the ratios $R_1$ and $R_2$ both fall within respective specific ranges indicative of the tobacco material T, judges that the image data shows the tobacco material T. On the other hand, if one of the ratios $R_1$ and $R_2$ is outside the corresponding specific range, the discrimination circuit 96 judges that the image data shows the foreign matter.

As described above, the discrimination circuit 96 detects foreign matter in the tobacco material T on the basis of the continuous image data obtained from the processing circuits 86, and therefore, foreign matter can be quickly detected, making it possible to increase the conveyance speed, namely, the treatment speed of the tobacco material T.

Also, the discrimination circuit 96 may treat the image data $D1_n$, $D2_n$ and $D3_n$ as a false RGB signal and the determination results may be displayed as a false color image on a display device (not shown).

The present invention is not limited to the foregoing embodiment alone and may be modified in various ways.

Figure 9:
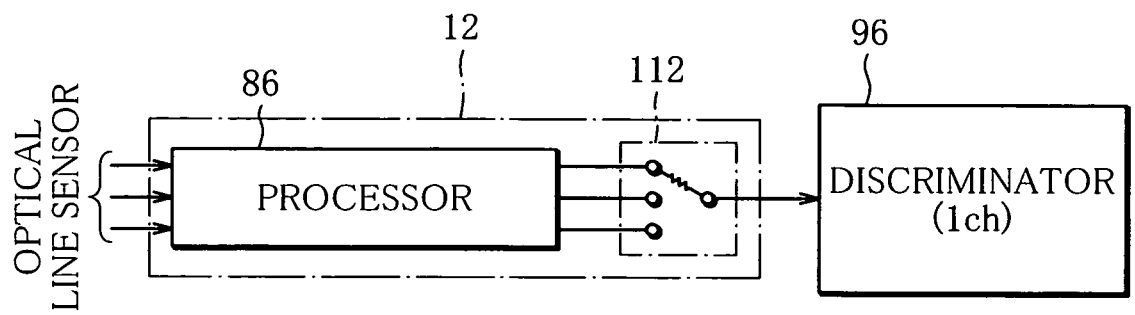
FIG. 9 illustrates a modification of a signal converter.

For example, in the above embodiment, the discrimination circuit 96 is adapted to receive the three parallel outputs of the signal converter 12. Alternatively, as shown in FIG. 9, the signal converter 12 may further include a switching circuit 112 connected between the processing circuits 86 and the discrimination circuit 96 for serially supplying the three outputs of the processing circuits 86 to the discrimination circuit 96. In this case, the discrimination circuit 96 detects foreign matter in the tobacco material T on the basis of each output from the processing circuits 86 and the determination results are successively displayed as monochromatic images on the display device.

Figure 10:
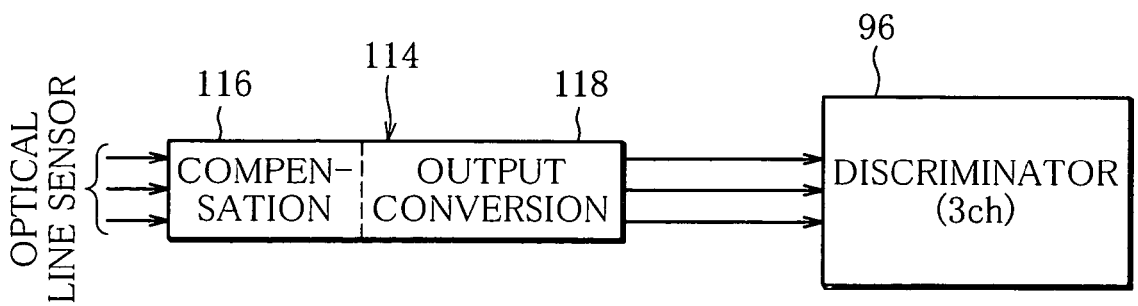
FIG. 10 illustrates a modification of the processing circuit.
Figure 11:
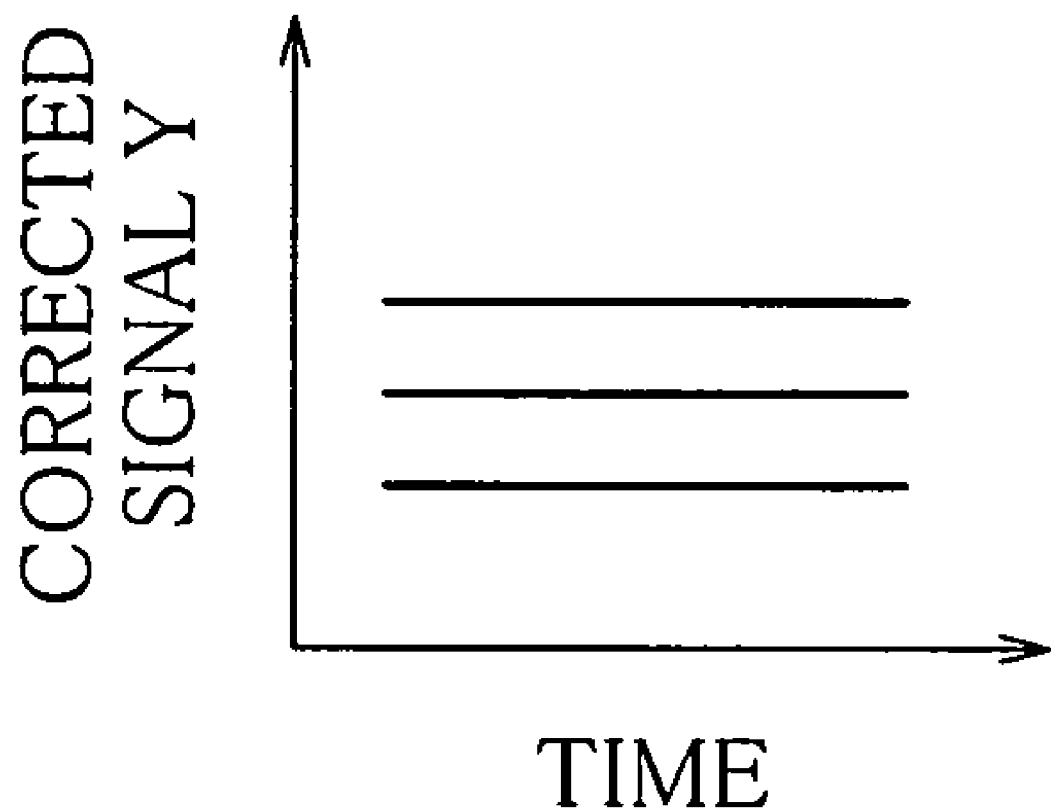
FIG. 11 illustrates an output conversion function of the processing circuit.

Further, each processing circuit 86 may be replaced with a processing circuit 114 shown in FIG. 10. The processing circuit 114 is equipped, besides the function 116 of correcting the electrical signals X from the optical line sensors 72, 78 and 84 to obtain the corrected signals Y, with an output conversion function 118 whereby the output of the corrected electrical signals Y to the discrimination circuit 96 is continued for a predetermined time, as shown in FIG. 11. In this case, while the conveyance of the tobacco material T is stopped, the discrimination circuit 96 can detect foreign matter in a given spot area of the tobacco material T in like manner.

The foregoing embodiment is based on the assumption that the tobacco material T is a mixture of tobacco leaves and foreign matter. The identification system of the present invention can also be used to detect foreign matter admixed in materials other than tobacco leaves, as well as to identify a specific component in a mixture or composite material comprising a plurality of different components.

FIG. 12 illustrates, by way of example, the spectral reflectance characteristics of wakame seaweed, or *Undaria pinnatifida*, and foreign elements that can possibly be admixed in cropped wakame, more specifically, green and gray fishing guts. The graph also shows the first to third wavelengths (1300 nm, 1730 nm, 1940 nm) of infrared light suited for the detection of the foreign elements in wakame.

It is clear from FIG. 12 that, with respect to the third wavelength of infrared light, there is no clear difference between the reflectance of wakame and those of the foreign elements, but with respect to the first and second wavelengths, wakame shows reflectance significantly different from those of the foreign elements. Thus, the discrimination circuit 60 obtains the aforementioned ratios $R_1(=D1_n/D3_n)$ and $R_2(=D2_n/D3_n)$ of the image data, whereby the foreign elements admixed in wakame can be detected with accuracy on the basis of the ratios $R_1$ and $R_2$.

FIG. 13 shows the spectral reflectance characteristics of composite materials, namely, a diaper and a sanitary item, and components (paper, nonwoven fabric, polymer) forming the composite materials, together with the first to third wavelengths (1600 nm, 1750 nm, 1940 nm) of infrared light suited for the identification of the components.

It is clear from FIG. 13 that the composite materials or their components show clear differences in reflectance at the first to third wavelengths of infrared light. The discrimination circuit can therefore identify the arrangement and distribution of the components constituting the individual composite materials, making it possible to manage the quality of products on the basis of the identification results.

As will be noted from the foregoing description of the embodiment, the third wavelength (1940 nm) of infrared light is used in common for the detection of foreign matter in materials and for the identification of components in composite materials. This is because the third wavelength of infrared light is absorbed well by water contained in materials and thus is useful in distinguishing materials containing water from those not containing water.

Also, the identification system of the present invention may use, in combination with the third wavelength of infrared light, wavelengths other than the aforementioned first and second wavelengths. Further, the number of wavelengths to be used is not limited to three. In cases where many kinds of foreign elements need to be detected or many kinds of target materials need to be identified, four or more different wavelengths of infrared light may of course be used in combination.

The invention claimed is:

1. A mixture identification system comprising:

conveying means for conveying a mixture along a predetermined conveyance path, the mixture containing a plurality of different materials of nearly identical color;

an irradiation device including an inspection line extending across the conveyance path, wherein said irradiation device includes a pair of lamp units for irradiating infrared light onto the inspection line, the lamp units being arranged upstream and downstream, respectively, of the inspection line as viewed in a conveying direction of the mixture, and wherein each of the lamp units includes a straight tube-type halogen lamp extending parallel with the inspection line and adapted to emit the infrared light, and a reflector for reflecting the infrared light from the halogen lamp toward the inspection line, said irradiation device being adapted to irradiate infrared light toward the mixture located on the inspection line;

an infrared camera device for receiving the infrared light reflected from the mixture and outputting image data of the mixture based on the received infrared light; and a discrimination circuit for identifying a target material contained in the mixture, based on the output from said infrared camera device, wherein said infrared camera device includes a spectral mirror for separating the received infrared light into light beams of respective different wavelength regions, a plurality of infrared filters for receiving the respective light beams and allowing only infrared light with respective specific wavelengths to pass therethrough, the specific wavelengths of infrared light causing the materials contained in the mixture to show a predetermined difference in reflectance when irradiated onto the mixture and reflected by the respective materials, and a plurality of optical line sensors for receiving the infrared light beams passed through the respective infrared filters, each of the optical line sensors including a large number of light receiving elements so arranged as to receive the infrared light reflected from the mixture on the inspection line and individually generating, as the image data, electrical signals corresponding to amounts of the infrared light received.

2. The mixture identification system according to claim 1, wherein said infrared camera device further includes a compensation circuit for compensating for a difference in sensitivity between the light receiving elements of each of the optical line sensors, and wherein the compensation circuit has gains and offset values set with respect to the individual light receiving elements to correct the electrical signals from the respective light receiving elements.

3. The mixture identification system according to claim 2, wherein said infrared camera device further includes a calibration plate capable of uniformly reflecting infrared light, and a guide for guiding movement of the calibration plate between an operative position located on the inspection line and a rest position remote from the inspection line.

4. The mixture identification system according to claim 2, wherein said irradiation device includes a pair of lamp units for irradiating infrared light onto the inspection line, the lamp units being arranged upstream and downstream, respectively, of the inspection line as viewed in a conveying direction of the mixture.

5. The mixture identification system according to claim 4, wherein each of the lamp units includes a straight tube-type halogen lamp extending parallel with the inspection line and adapted to emit the infrared light, and a reflector for reflecting the infrared light from the halogen lamp toward the inspection line.

6. The mixture identification system according to claim 5, wherein said irradiation device further includes a lamp housing containing the pair of lamp units and having an opening for allowing the infrared light emitted from the pair of lamp units to pass therethrough toward the inspection line, a glass window closing the opening and allowing the infrared light to transmit therethrough, and a cooling unit for cooling air in the lamp units.

7. The mixture identification system according to claim 6, wherein the cooling unit supplies cooling air into the lamp units and keeps pressure in the lamp units higher than external pressure.

8. The mixture identification system according to claim 7, wherein said irradiation device further includes an air injection unit for producing a flow of air along an outer surface of the glass window.

9. The mixture identification system according to claim 6, wherein said irradiation device further includes a slide mechanism permitting the pair of lamp units to be pulled out of the lamp housing, the slide mechanism supporting the pair of lamp units in such a manner that the lamp units are slidable in a direction parallel with the inspection line.

10. The mixture identification system according to claim 1, wherein said irradiation device further includes a lamp housing containing the pair of lamp units and having an opening for allowing the infrared light emitted from the pair of lamp units to pass therethrough toward the inspection line, a glass window closing the opening and allowing the infrared light to transmit therethrough, and a cooling unit for cooling air in the lamp units.

11. The mixture identification system according to claim 10, wherein the cooling unit supplies cooling air into the lamp units and keeps pressure in the lamp units higher than external pressure.

12. The mixture identification system according to claim 11, wherein said irradiation device further includes an air injection unit for producing a flow of air along an outer surface of the glass window.

13. The mixture identification system according to claim 1, wherein said infrared camera device further includes a compensation circuit for compensating for a difference in sensitivity between the light receiving elements of each of the optical line sensors, and wherein the compensation circuit has gains and offset values set with respect to the individual light receiving elements to correct the electrical signals from the respective light receiving elements.

14. The mixture identification system according to claim 13, wherein said infrared camera device further includes a calibration plate capable of uniformly reflecting infrared light, and a guide for guiding movement of the calibration plate between an operative position located on the inspection line and an inoperative position remote from the inspection line.

* * * * *